US00PP20686P2

(12) United States Plant Patent
Hanes

(10) Patent No.: US PP20,686 P2
(45) Date of Patent: Jan. 26, 2010

(54) ***PELARGONIUM* PLANT NAMED 'CANTE ORAN'**

(50) Latin Name: *Pelargonium interspecific*
Varietal Denomination: Cante Oran

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,984

(22) Filed: Nov. 14, 2008

(51) Int. Cl.
*A01H 5/00* (2006.01)

(52) U.S. Cl. ..... Plt./327

(58) Field of Classification Search ..... Plt./327
See application file for complete search history.

*Primary Examiner*—Annette H Para
(74) *Attorney, Agent, or Firm*—S. Matthew Edwards

(57) ABSTRACT

A new *Pelargonium* plant named 'Cante Oran,' particularly distinguished by the red-orange color, semi-upright, outwardly spreading and mounding habit, dense and freely basal branching habit, dark green foliage, heat tolerance, and good edema resistance.

1 Drawing Sheet

Latin name of the genus and species of the plant claimed: *Pelargonium interspecific.*

Varietal denomination: 'Cante Oran'.

BACKGROUND OF THE NEW PLANT

The present invention comprises a new *Pelargonium* hybrid, botanically known as *Pelargonium interspecific,* more specifically as *Pelargonium hortorum* times *Pelargonium tongaense*, hereinafter referred to by the variety name 'Cante Oran.'

'Cante Oran' is a product of a planned breeding program. The new cultivar 'Cante Oran' has red-orange color, semi-upright, outwardly spreading and mounding habit, dense and freely basal branching habit, dark green foliage, heat tolerance, and good edema resistance.

'Cante Oran' originated from a hybridization in a controlled breeding program in Gilroy, Calif. U.S.A. The female parent was an unpatented *Pelargonium interspecific* hybrid seedling identified as '10263-10' with scarlet color. '10263-10' has less vigor, a more open habit, and darker foliage than 'Cante Oran.'

The male parent of 'Cante Oran' was an unpatented *Pelargonium interspecific* hybrid seedling identified as '10279-10' with orange color. '10279-10' has a more open habit, less vigor, and less floriferiousness than 'Cante Oran.'

'Cante Oran' was selected as one flowering plant within the progeny of the stated cross in August 2006 in a controlled environment in Gilroy, Calif. U.S.A. The pollination took place in April 2006 and the seed sowing in June 2006.

The first act of asexual reproduction of 'Cante Oran' was accomplished when vegetative cuttings were taken from the initial selection in the August 2006 in a controlled environment in Gilroy, Calif. U.S.A.

Horticultural examination of plants grown from cuttings of the plant initiated in August 2006 in Gilroy, Calif. U.S.A., and continuing thereafter, has demonstrated that the combination of characteristics as herein disclosed for 'Cante Oran' are firmly fixed and are retained through successive generations of asexual reproduction.

'Cante Oran' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cante Oran' has not been made publicly available more than one year prior to the filing of this application.

DESCRIPTION OF THE DRAWINGS

The accompanying photographic drawing shows typical flower and foliage characteristics of 'Cante Oran' with colors being as true as possible with an illustration of this type. The photographic drawing shows three flowering potted plants of the new variety in a hanging basket and a close-up of the flowers. The basket was grown and photographed outside in Gilroy, Calif. U.S.A. in July 2008, and the plants were about 3–4 months old. The plant used for the close-up photograph was grown and photographed in a greenhouse in October 2007 and was about 2 months old.

DETAILED BOTANICAL DESCRIPTION

The measurements were taken in Gilroy, Calif. U.S.A., in October 2008 on plants that were growing in 8 inch plastic pots in a greenhouse. Culture of these plants started in about August 2008 and the plants were about 2 months old.

Color chart used: Royal Horticultural Society Colour Chart (R.H.S.) 2001

BRIEF SUMMARY OF INVENTION

The following observations, measurements, and comparisons describe plants grown outside in Gilroy, Calif. U.S.A. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY 'CANTE ORAN' AND A SIMILAR VARIETY

| | 'Cante Oran' | 'Cante Coras' (U.S. Plant Pat. No. 15,653) |
|---|---|---|
| Flower color, size | RHS 44B, narrow petals | RHS 50A, fuller petals |
| Petiole size | Shorter | Longer |
| Peduncle size | Shorter | Longer |
| Sepal size | Shorter | Longer |

Plant:

*Form, growth and habit.*—Semi-upright, outwardly spreading and mounding habit, dense habit, freely basal branching habit.

*Plant height.*—10–12 cm.

*Plant height (inflorescence included).*—12–13 cm.

*Plant width.*—15–18 cm.

Foliage:

*Arrangement.*—Alternate.

*Immature, leaf color, upper surface.*—RHS 146A.

*Lower surface.*—RHS 147B.

*Mature, leaf color, upper surface.*—RHS 147A.

*Lower surface.*—RHS 147B.

*Length.*—7.0–7.2 cm.

*Width.*—7.4–7.6 cm.

*Shape.*—Orbicular.

*Base shape.*—Reniform.

*Apex shape.*—Mucronulate.

*Margin.*—Crenate.

*Texture.*—Hirsute.

*Color of zone.*—Slightly darker than RHS 147A.

*Width of zone.*—0.5 cm.

*Color of veins, upper surface.*—Indistinct.

*Color of veins, lower surface.*—Slightly lighter than RHS 147B.

*Petioles color.*—RHS 144A.

*Petioles length.*—5.0–5.1 cm.

*Diameter of petiole.*—0.2 cm.

*Texture.*—Hirsute.

Stem:

*Color of stem.*—RHS 144A.

*Length of stem.*—5.0–5.4 cm.

*Diameter.*—0.6 cm.

*Length of internodes.*—0.5–0.8 cm.

*Texture.*—Hirsute.

Inflorescence:

*Type.*—An umbel composed of 10–14 flowers and buds.

*Color of peduncle.*—RHS 144A.

*Length of peduncle.*—7.0–7.2 cm.

*Peduncle diameter.*—0.2 cm.

*Texture.*—Hirsute; few pilose.

*Color of pedicel.*—RHS 187A but a little lighter.

*Length of pedicel.*—3.0–3.2 cm.

*Diameter of pedicel.*—0.1 cm.

*Texture.*—Hirsute.

*Umbel diameter.*—7.0–8.0 cm.

*Umbel depth.*—4.5–4.9 cm.

*Number of umbels per plant.*—2.

*Duration of flowering.*—Continuous flowering throughout the summer.

*Lastingness of flowers.*—About 1 week.

Corolla:

*Form.*—Single; polypetalous, composed of 5 petals, lower petals do not overlap.

*Length of flower.*—4.0–4.4 cm.

*Width of flower.*—4.3–4.5 cm.

*Color upper petals, upper surface.*—RHS 44B; RHS 60A basal veins.

*Color upper petals, lower surface.*—RHS 43B.

*Length of upper petals.*—2.3–2.4 cm.

*Width of upper petals.*—1.3–1.4 cm.

*Color lower petals, upper surface.*—RHS 44B.

*Color lower petals, lower surface.*—RHS 43B.

*Length of lower petals.*—2.2–2.3 cm.

*Width of lower petals.*—1.5–1.7 cm.

*Petal shape.*—Slightly spathulate to obovate.

*Apex shape.*—Rounded.

*Margin.*—Entire.

*Petal texture.*—Papillose on both surfaces.

Bud (just before opening):

*Color.*—RHS 44A.

*Length.*—1.4–1.6 cm.

*Width.*—0.7 cm.

*Shape.*—Ovate.

Calyx:

*Number of sepals.*—5.

*Color of sepals.*—RHS 146A; anthocyanins of slightly RHS 187B basally.

*Length of sepals.*—0.7–0.8 cm.

*Width of sepals.*—0.3–0.35 cm.

*Sepal shape.*—Lanceolate.

*Apex shape.*—Acute.

*Margins.*—Entire.

*Texture.*—Hirsute; few pilose.

Reproductive organs:

*Pistil.*—1.

*Length.*—0.5 cm.

*Style color.*—Slight hue of RHS 45C.

*Style length.*—0.2 cm.

*Stigma color.*—Slight hue of RHS 45C.

*Number of stamens.*—4–6.

*Color of filaments.*—RHS N155B but whiter basally; RHS 45C at the anther.

*Length filaments.*—0.2–0.3 cm.

*Anther color.*—RHS 46B.

*Color of pollen.*—RHS 25B.

*Pollen amount.*—Moderate.

*Fertility/seed set.*—Not observed on this hybrid.

Disease/pest resistance: Disease resistance or susceptibility has not been observed on this hybrid.

What is claimed is:

1. A new and distinct variety of *Pelargonium* plant named 'Cante Oran,' substantially as illustrated and described herein.

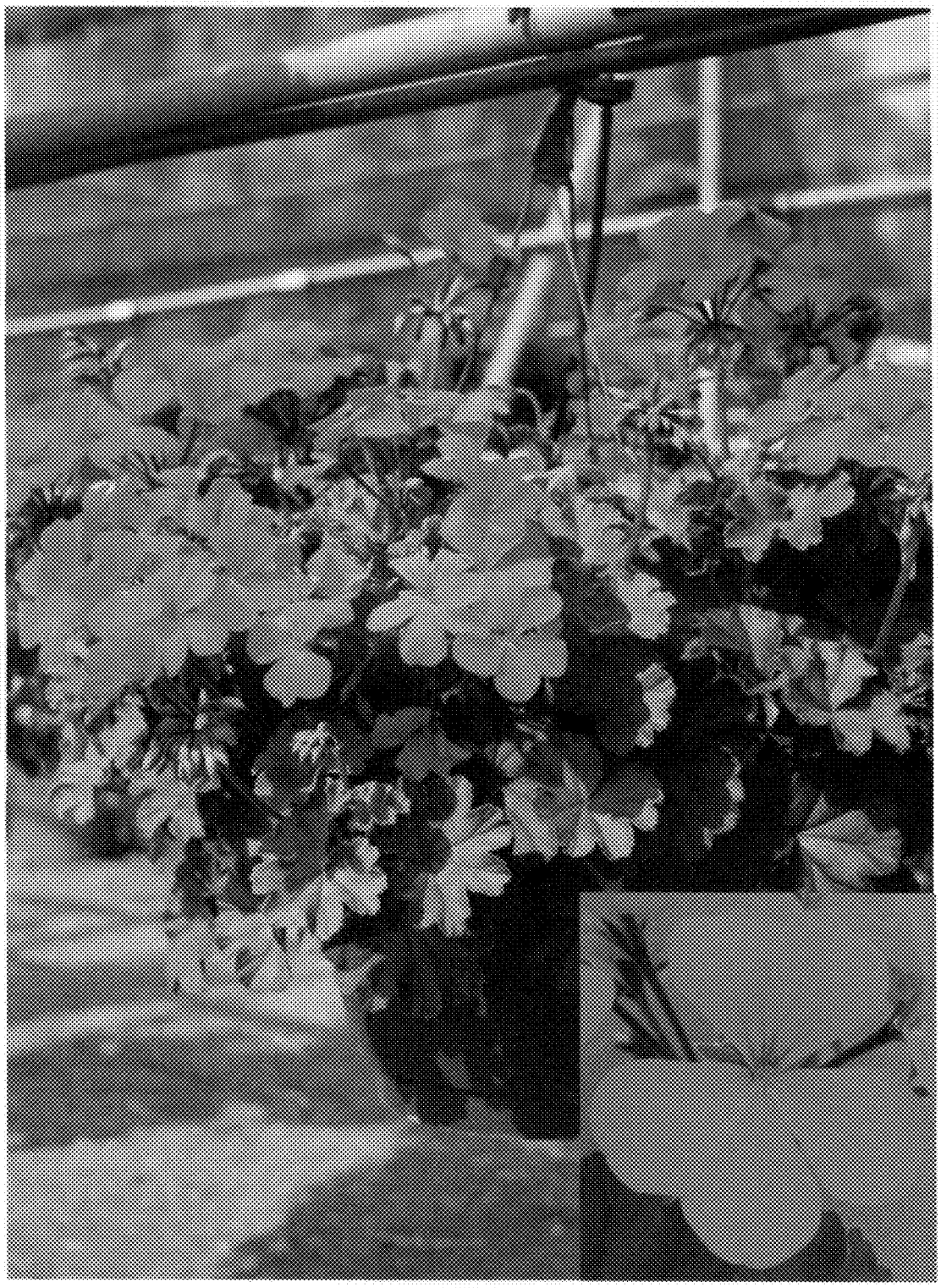

* * * * *